United States Patent [19]

Shimamatsu et al.

[11] 4,021,304

[45] May 3, 1977

[54] PROCESS FOR CONTINUOUS CULTIVATION OF PROTEIN-PRODUCING MICROORGANISMS

[75] Inventors: Hidenori Shimamatsu; Masaharu Yamada, both of Chiba; Toshio Tanaka, Ichihara; Yahiko Suzuki, Ichikawa, all of Japan

[73] Assignees: Dainippon Sugar Manufacturing Co., Ltd.; Dainippon Ink and Chemicals, Incorporated, both of Tokyo, Japan

[22] Filed: May 16, 1974

[21] Appl. No.: 462,065

[30] Foreign Application Priority Data

Apr. 19, 1973 Japan .............................. 48-43618

[52] U.S. Cl. ............................... 195/28 R; 195/32; 195/37; 195/49; 195/82; 195/115; 195/118

[51] Int. Cl.² .......................................... C12B 1/00

[58] Field of Search .............. 195/32, 37, 28 R, 49, 195/82, 115, 117, 118, 108, 109

[56] References Cited

UNITED STATES PATENTS

| | | | |
|---|---|---|---|
| 2,822,319 | 2/1958 | Monod | 195/115 |
| 3,672,953 | 6/1972 | Coty et al. | 195/115 X |

*Primary Examiner*—R. B. Penland
*Attorney, Agent, or Firm*—Sherman & Shalloway

[57] ABSTRACT

A process for continuous cultivation of microorganisms capable of producing protein while adjusting the pH of the culture broth to a constant value with ammonia, characterized in that the growth rate of the microorganisms is maintained constant by maintaining the rate of consumption of ammonia constant.

3 Claims, No Drawings

PROCESS FOR CONTINUOUS CULTIVATION OF PROTEIN-PRODUCING MICROORGANISMS

This invention relates to a continuous process for cultivating a protein producing microorganisms (which may often be called SCP hereinafter).

Generally, in the continuous cultivation of SCP, it is necessary to maintain the growth rate constant, and the detection of the growth rate of SCP during continuous cultivation has been regarded as essential for maintaining and controlling the cultivation of microorganisms used in the production of protein. Thus, in the conventional continuous SCP cultivation, it has been the practice to measure the dry weight of the cells, and calculate the growth rate of the cells from the measured dry weight. Known methods for measuring the dry weight of cells include, for example, a microcscopic method wherein the number of living cells in a sample prepared from the culture broth is counted directly using a microscope, a spectrophotometric method wherein the cells are suspended in a suitable solvent, measuring the absorbance of the suspension by a spectrophotometer, and converting the absorbance value to the dry weight of the cells, and a weighing method wherein the sample is centrifugally concentrated, and dried, after which the dried cells are weighed. However, intrinsically, it is unreasonable to use a far smaller amount of the sample than the culture broth contained in a large amount in a large-volume fermentor as a representative sample, and moreover, the measurement can be done only intermittently. Therefore, even when fluctuations occur in the measured values, it is difficult to determine rapidly whether the fluctuations are due to changes in the state of cultivation, and pertinent measures to be taken to cope with any changes would be delayed.

In addition, various troubles occur according to the types of the carbon sources used for cultivation. For example, when molasses is used as a sole carbon source, the color of the molasses or colloidal substances present therein adversely affect the measured values determined by the spectrophotometric method or the weighing method described above. When a hydrocarbon is used as a carbon source, the measurement of the dry weight of cells by the microscopic method and the spectrophotometric method often meets with difficulties because of the tendency of the cells to coagulate. Also, the measurement by the weighing method gives somewhat greater measured values and cause errors unless the hydrocarbon adhering to the cells is removed sufficiently.

An object of this invention is to provide a process for continuously cultivating single cell protein, which is free from the defects of the conventional methods described above, and permits a rapid and accurate controlling action.

Investigations have been conducted to achieve this object, and led to the discovery that when the rate of consumed ammonia is constant during the continuous cultivation of protein producing microorganisns performed while adjusting the pH of the culture broth to a specific value, the growth rate of the protein producing microorganism becomes constant, and when the rate of ammonia consumption varies, the growth rate of SCP changes, and that when the fluctuated rate of ammonia consumption is returned to the original rate, the growth rate of SCP also returns to the original rate.

According to this invention, therefore, there is provided a process for continuously cultivating a protein producing microorganism while adjusting the pH of the culture broth to a constant value with ammonia, characterized in that the growth rate of the single cell protein is maintained constant by maintaining the rate of consumption of ammonia constant.

As a result of maintaining the rate of consumption of ammonia constant, the growth rate of the microorganism can be maintained constant. It is not necessary, therefore, to take the trouble of measuring the amount of the microorganism in the culture broth in order to determine whether the growth rate of the microorganism is constant or not. Furthermore, according to this invention, the rate of consumption of ammonia can be controlled always mechanically outside the fermentor, and therefore, it is not necessary to sample a specimen from the fermentor for measurement. Thus, all of the difficulties of the conventional methods can be overcome by the process of this invention, and there is no fear of infection of the culture medium with unfavourable microbes at the time of sampling.

It is known to use ammonia in the cultivation of protein producing microorganism in order to adjust the pH of the culture medium, or supply nitrogen to the fermentor, but there has been no prior example in which the rate of consumption of ammonia is precisely detected, and is combined positively with the adjustment of the growth rate of the protein producing microorganism.

The use of sodium hydroxide for the pH adjustment of the culture broth is also conventional. However in this case, it is necessary to add an ammonium salt or urea, etc. as a nitrogen source, and therefore, it is extremely difficult from the viewpoint of operation to control the growth rate of the protein producing microorganism on the basis of the consumption rate of sodium hydroxide. Furthermore, the protein content of the cells obtained as final product is not stable.

The sole carbon source used in the process of this invention may be any substance that can usually be used for cultivating protein producing microorganisms, some examples of which are carbon dioxide, carbohydrates, alcohols, fatty acids, organic acids, and hydrocarbons. The hydrocarbons such as n-paraffin, and the alcohols such as ethanol are especially suitable. In addition to the carbon source, nitrogen sources and inorganic salts, or other optional additives, such as traces of minerals, amino acids, vitamins, or organic nitrogen, can be employed in a customary manner.

One preferred embodiment of this invention will be described in detail below.

Seed cells are inoculated in a culture medium containing the carbon source, nitrogen source, inorganic salts, etc. described above, and cultivated while adjusting the pH of the culture medium to a constant value using ammonia. When the cultivation proceeds and then changes from a batchwise cultivation to a continuous cultivation, and the continuous supply of the culture medium and the continuous withdrawal of the culture broth containing the cultivated cells are begun, the rate of consumption of ammonia required to maintain the pH at a predetermined value fluctuates in the early stage from a predetermined value, but soon becomes stable at the predetermined value. This shows that the growth rate of the protein producing microorganism is steady. The time required from the beginning of continuous cultivation until the growth rate of the microorganism becomes steady depends mainly upon the type of the seed cells, the culturing age at the time of changing to the continuous cultivation, the type and scale of the fermentor, and the composition of the culture medium. When the rate of ammonia consumption changes and therefore, the growth rate of the microorganism varies during the continuous cultivation of the microorganism, suitable measures are taken according to the cause of the change so that the rate of ammonia consumption returns to the original rate and thus the rate of growth of the producing microorganism protein becomes constant. The cause of fluctuation that can be conceived include, for example, changes in the temperature, the pressure, the aeration rate, and the amount of the culture broth, etc. within the fermentor.

Ammonia to be used in this invention may be in any form, such as gaseous ammonia, liquid ammonia or ammonia solution. The amount of ammonia consumed is detected by using a conventional flowmeter, or by measuring a decrease in the volume or weight of the liquid within a storage vessel. Other measuring means can also be used if they permit continuous measurement and high precision. The rate of consumption of ammonia which becomes a measure for controlling the cultivation in accordance with this invention means the amount of ammonia consumed which is measured every 10 minutes to 2 hours. If the time interval of measurement is shorter than 10 minutes, the fluctuation becomes greater, and if the time interval is longer than 2 hours, there is some time lag until there is an influence on the measured amount of ammonia consumed, even if there is a change in temperature, pressure, the aeration rate, and the amount of the culture broth in the fermentor. Consequently, delay occurs in taking measures, and it is difficult to perform a stable control of cultivation. Accordingly, it is preferred that the amount of ammonia consumed should be observed preliminarily every 30 to 60 minutes, and the time interval in which the fluctuation is minimum should be selected for measurement. This will lead to a good control of cultivation.

The process of this invention can be performed, for example, by using an automatic apparatus including a pH detector within the fermentor, and a pH determining member, an ammonia flow rate controlling member and an ammonia flow rate recording member outside the fermentor which are interlocked with one another. If the specification of the cultivating apparatus can be known, control systems for the temperature, the pressure, the amount of aeration, and the amount of liquid can also be interlocked with this automatic apparatus, and the entire cultivation process can be controlled automatically.

The following Examples and Comparative Example illustrate the present invention in greater detail.

EXAMPLE 1

After performing batchwise cultivation for 12 hours in a 1000-liter volume fermentor equipped with an agitator at a speed of 300 rpm using 20 Kg/m$^3$ of n-paraffin as a carbon source, the continuous cultivation of a yeast of Candida species was performed for 240 hours at a pH of 4.5 and a temperature of 35° C. while inspecting the amount of ammonia consumed. During this time, the aeration rate was maintained at 0.7 vvm and the rate of feeding the culture medium at 120 liters/hour, and also the amount of the culture broth in the fermentor was 600 liters. The consumed rate of aqueous ammonia (25% by weight) measured every 30 minutes was 1.4 Kg/m$^3$.hr., and the growth rate of the cell mass was 3.0 Kg/m$^3$.hr. Thus, a complete steady state was maintained.

Immediately after the lapse of 240 hours from the initiation of the continuous cultivation, the cultivation temperature was lowered to 23° C., and then the cultivation was continued for 72 hours. During this time, the rate of aqueous ammonia consumed was 0.7 Kg/m$^3$.hr., and the rate of growth of the cell mass was 1.5 Kg/m$^3$.hr. Immediately after the lapse of 72 hours from the time when the temperature was lowered to 23° C., the temperature was again returned to 35° C., whereupon the rate of consumption of aqueous ammonia and the rate of growth of the cell mass were returned to the original.

Table 1 shows the results obtained. The growth rate of the cell mass was measured by the weighing method.

Table I

| Time that elapsed after the initiation of continuous cultivation (hours) | Temperature (° C.) | Rate of consumption of 25 % by weight aqueous ammonia (Kg/m$^3$ . hr) | Growth rate of cell mass (Kg/m$^3$ . hr.) | Crude protein content in the harvested cells(%) |
|---|---|---|---|---|
| 48 | 35 | 1.40 | 3.0 | 60.2 |
| 72 | 35 | 1.42 | 3.0 | 61.1 |
| 96 | 35 | 1.40 | 3.0 | 60.8 |
| 120 | 35 | 1.40 | 2.9 | 60.8 |
| 144 | 35 | 1.39 | 3.0 | 60.6 |
| 168 | 35 | 1.40 | 3.0 | 59.8 |
| 192 | 35 | 1.41 | 3.1 | 60.1 |
| 216 | 35 | 1.40 | 3.1 | 58.7 |
| 240 | 35 | 1.40 | 3.0 | 59.5 |
| 264 | 23 | 0.71 | 1.5 | 60.3 |
| 288 | 23 | 0.70 | 1.5 | 61.2 |
| 312 | 23 | 0.70 | 1.6 | 61.2 |
| 336 | 35 | 1.39 | 2.9 | 60.5 |
| 360 | 35 | 1.40 | 3.0 | 60.1 |

EXAMPLE 2

After performing batchwise cultivation for 12 hours in the same fermentor as used in Example 1 using 33 Kg/m$^3$ of ethanol as a carbon source, the continuous cultivation of a yeast of Pichia species was performed for 240 hours at a pH of 4.5 and a temperature of 34° C. while inspecting the amount of ammonia consumed. The amount of the culture broth in the continuous cultivation was 600 liters, and the amount of aeration and the rate of feeding the culture medium were 0.7 vvm, and 120 liters/hour, respectively. During this time, the rate of gaseous ammonia (99.9%) consumed which was measured every 60 minutes was 0.35 Kg/m$^3$.hr., and the growth rate of the cell mass was 3.1 Kg/m$^3$.hr. Thus, a complete steady state was maintained.

The results obtained are shown in Table 2. The growth rate of the cell mass was measured by the weighing method.

Table 2

| Time that elapsed after the initiation of the continuous cultivation (hours) | Rate of gaseous ammonia consumed (Kg/m$^3$ . hr.) | Growth rate of the cell mass (Kg/m$^3$ . hr.) |
| --- | --- | --- |
| 48 | 0.34 | 3.1 |
| 72 | 0.35 | 3.2 |
| 96 | 0.35 | 3.1 |
| 120 | 0.36 | 3.1 |
| 144 | 0.35 | 3.1 |
| 168 | 0.34 | 3.2 |
| 192 | 0.35 | 3.2 |
| 216 | 0.35 | 3.1 |
| 240 | 0.35 | 3.3 |

Comparative Example 1

A yeast of Candida species was cultivated continuously in the same fermentor as used in Example 1 using 600 liters of a culture medium containing 20 Kg/m$^3$ of n-paraffin as a carbon source and 12 Kg/m$^3$ of ammonium sulfate as a nitrogen source at a pH of 4.5 and a temperature of 35° C. while maintaining the amount of aeration at 0.7 vvm. For the adjustment of the pH of the culture medium, a 50% aqueous solution of sodium hydroxide was used. The results obtained are shown in Table 3. The growth rate of the cell mass was measured by the weighing method.

Table 3

| Time that elapsed after initiaton of the continuous cultivation (hours) | Rate of consumption of 50 % aqueous solution of sodium hydroxide (Kg/m$^3$ . hr) | Growth rate of the cell mass (Kg/m$^3$ . hr) | Content of crude protein (%) |
| --- | --- | --- | --- |
| 48 | 2.4 | 3.0 | 59 |
| 72 | 1.8 | 2.4 | 60 |
| 96 | 2.2 | 2.2 | 59 |
| 120 | 1.3 | 2.8 | 56 |
| 144 | 1.9 | 2.7 | 54 |
| 168 | 1.4 | 3.0 | 54 |
| 192 | 2.0 | 3.2 | 57 |
| 216 | 2.5 | 2.5 | 58 |
| 240 | 1.7 | 3.1 | 55 |

It is seen from Table 3 that in this comparative experiment, the rate of consumption of the aqueous solution of sodium hydroxide was not stable, and the growth rate of the cell mass and the crude protein content of the cell fluctuated during the time, making it impossible to maintain the cultivation in the steady state.

What we claim is:

1. In a process for the continuous cultivation of a single cell protein producing microorganism at a constant growth rate in a culture broth containing a carbon source selected from the group consisting of hydrocarbons, alcohols, carbohydrates, carbon dioxide and organic acids in which the pH of the culture broth is maintained at a constant valve by the addition of ammonia the improvement which comprises (1) maintaining the constant growth rate of said protein producing microorganism by adding ammonia at a constant rate and amount under steady state conditions of temperature, pressure, rate of aeration and amount of culture broth (2) measuring the rate of ammonia consumed at time intervals of from 10 to 120 minutes throughout the fermentation; thereby determining any variation in the rate of ammonia consumed at said selected time intervals and then upon determining said variation adjusting the cultivation conditions of temperature, pressure, rate of aeration and amount of culture broth back to said steady state.

2. The process of claim 1 wherein said single cell protein is a yeast of Candida species.

3. The process of claim 1 wherein said single cell protein is a yeast of Pichia species.

* * * * *